(12) United States Patent
Yamamoto et al.

(10) Patent No.: US 6,611,966 B1
(45) Date of Patent: Sep. 2, 2003

(54) GOGGLES

(75) Inventors: Tamenobu Yamamoto, Nishinomiya (JP); Tomihiro Funamoto, Nagaokakyo (JP); Kimio Matsumoto, Matsubara (JP)

(73) Assignee: Yamamoto Kogaku Co., Ltd., Osaka (JP)

( * ) Notice: Subject to any disclaimer, the term of this patent is extended or adjusted under 35 U.S.C. 154(b) by 0 days.

(21) Appl. No.: 09/789,994

(22) Filed: Feb. 21, 2001

(30) Foreign Application Priority Data

Feb. 22, 2000 (JP) ..................................... 2000-077272

(51) Int. Cl.[7] .................................................. A61F 9/02
(52) U.S. Cl. ........................................................ 2/436
(58) Field of Search ........................... 2/435, 436, 437, 2/431, 440

(56) References Cited

U.S. PATENT DOCUMENTS

| | | | | |
|---|---|---|---|---|
| 3,591,864 A | * | 7/1971 | Allsop | 2/14 |
| 3,945,044 A | * | 3/1976 | McGee et al. | 2/14 |
| 4,179,756 A | * | 12/1979 | Lucas | 2/434 |
| 4,290,673 A | * | 9/1981 | Yamamoto | 351/62 |
| 4,443,893 A | * | 4/1984 | Yamamoto | 2/436 |
| 5,671,483 A | * | 9/1997 | Reuber | 2/424 |

FOREIGN PATENT DOCUMENTS

| | | |
|---|---|---|
| DE | 30 05 048 | 11/1980 |
| DE | 196 45 432 | 5/1998 |

* cited by examiner

*Primary Examiner*—John J. Calvert
*Assistant Examiner*—Katherine Moran
(74) *Attorney, Agent, or Firm*—Koda & Androlia

(57) ABSTRACT

Goggles include an inner lens plate, an intermediate lens plate and an outer lens plate. A space between the inner and intermediate lens plates and a space between the intermediate and outer lens plates form heat-insulating layers. The intermediate lens plate has a through hole and at least one of the inner and outer lens plates has a vent hole. The vent hole is covered with a moisture blocking member which prevents moisture from passing and allows air to pass.

12 Claims, 6 Drawing Sheets

GOGGLES

FIELD OF THE INVENTION

The present invention relates to goggles, more particularly relates to goggles used for skiing or snowboarding.

PRIOR ART

Goggles of this type are used under very cold weather. Especially when a skier wearing goggles stops sliding, the inner surfaces of goggle lenses are clouded up due to the skier's body temperature, sweating or the like and an accident is likely to occur because of poor visibility.

To prevent such cloud up of goggle lenses, the following measures (a) and (b) have been conventionally taken:

(a) Method of applying chemical anti-fog treatment to the inner surfaces of goggle lenses This method provides a certain anti-fog effect when the temperature of the surface of the lens is down to about 0° C. or higher. However, in an environment where the temperature of the surface is below 0° C., the temperature of the inner surface side of lens plate also lowers below 0° C. and water drops produced on the inner surface of lens plate are frozen, and as a result, the treated lens cannot provide a sufficient anti-fog effect.

(b) Method of producing a goggle lens/lenses with two inner and outer lens plates to provide a heat-insulating layer between the inner and outer lens plates In this method, the heat insulating layer prevents the inner surface of the goggle lens from promptly becoming clouded up even when the temperature of the surface of the goggle lens is below 0° C. Therefore this method can provide an anti-fog effect even in an environment where the temperature of the surface of the outer lens plate is below 0° C. However, today's skiing or the like requires a very large quantity of motion, which intensely increase a skier's body temperature and enhance a skier's sweating. As a result, a farther higher anti-fog effect is required.

SUMMARY OF THE INVENTION

It is, therefore, an object of the present invention to provide goggles which prevent water drops on inner surface of goggle lens from easily becoming frozen and provides a very high anti-fog effect even if the temperature of the surface of goggle lens is below 0° C.

Goggles according to the present invention include three lens plates, i.e. inner, intermediate and outer lens plates and inner spaces between the inner and intermediate lens plates and the intermediate and outer lens plates are used as heat insulating layers.

Also, the goggles of the present invention may have a through hole in the intermediate lens plate and a vent hole in the inner and/or outer lens plates. Alternatively, without providing the through hole, vent holes may be formed respectively on the inner and outer lens plates and closed by a moisture blocking means which prevents moisture from passing and allows air to pass. The through hole and the vent hole are preferably provided at positions where the field of vision is not disturbed.

The distance between the adjacent lens plates of the goggles of the present invention may be 1.6 to 2.4 mm, and more preferably 2 mm.

The goggles of the present invention may include spacing frames between the inner and intermediate lens plates and between the intermediate and outer lens plates. And the contacting surfaces between the inner, intermediate and outer lens plates and the spacing frames may be bonded together.

DESCRIPTION OF THE PREFERRED EMBODIMENTS

Figure 1:
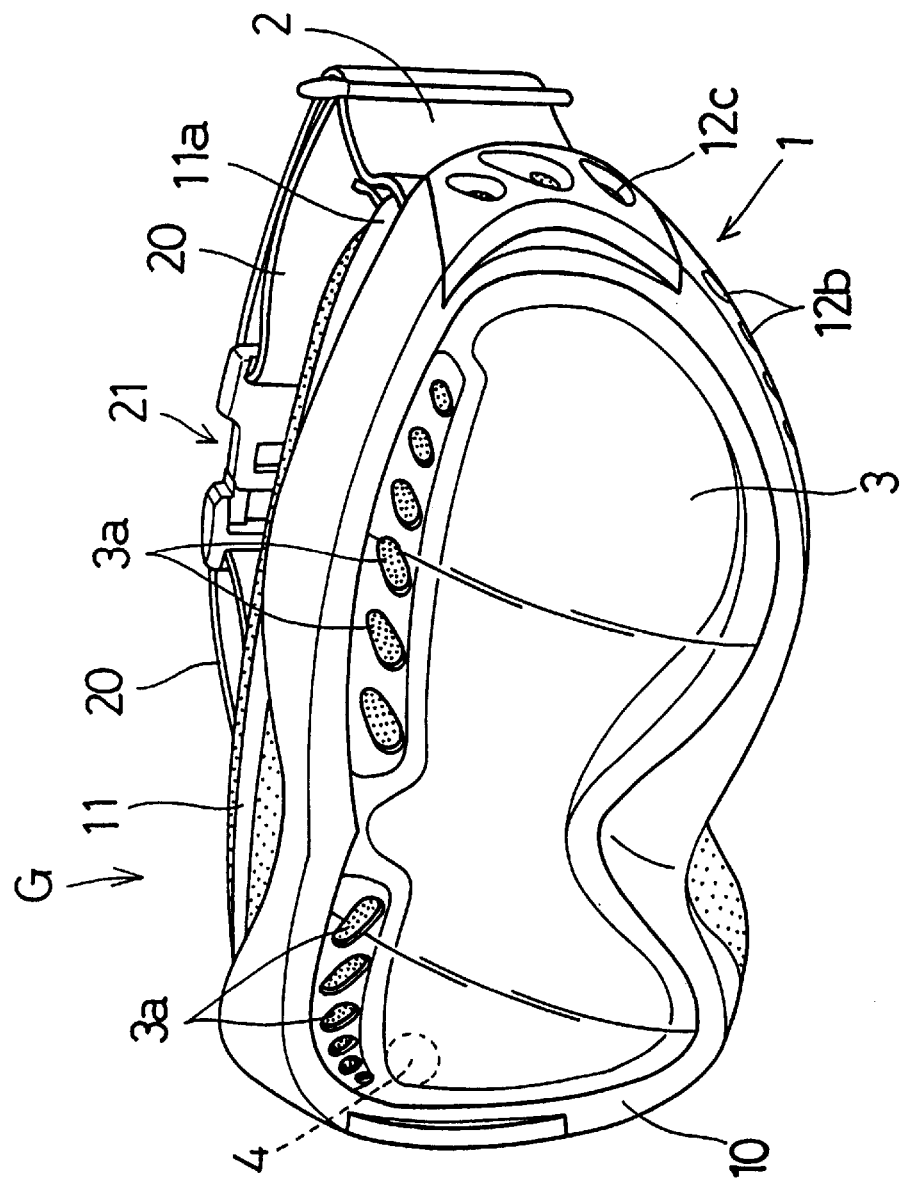
FIG. 1 is a perspective view of goggles in one embodiment of the present invention.
Figure 2:
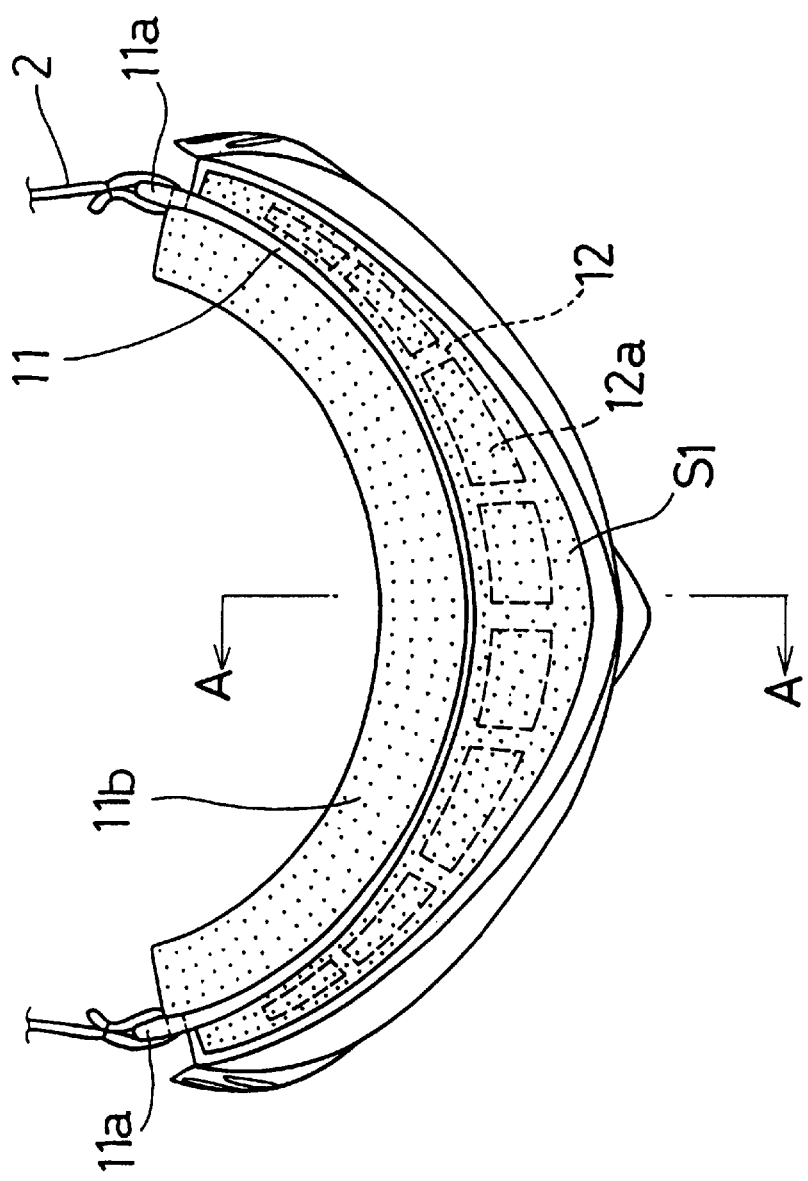
FIG. 2 is a top view of the goggles.
Figure 5:
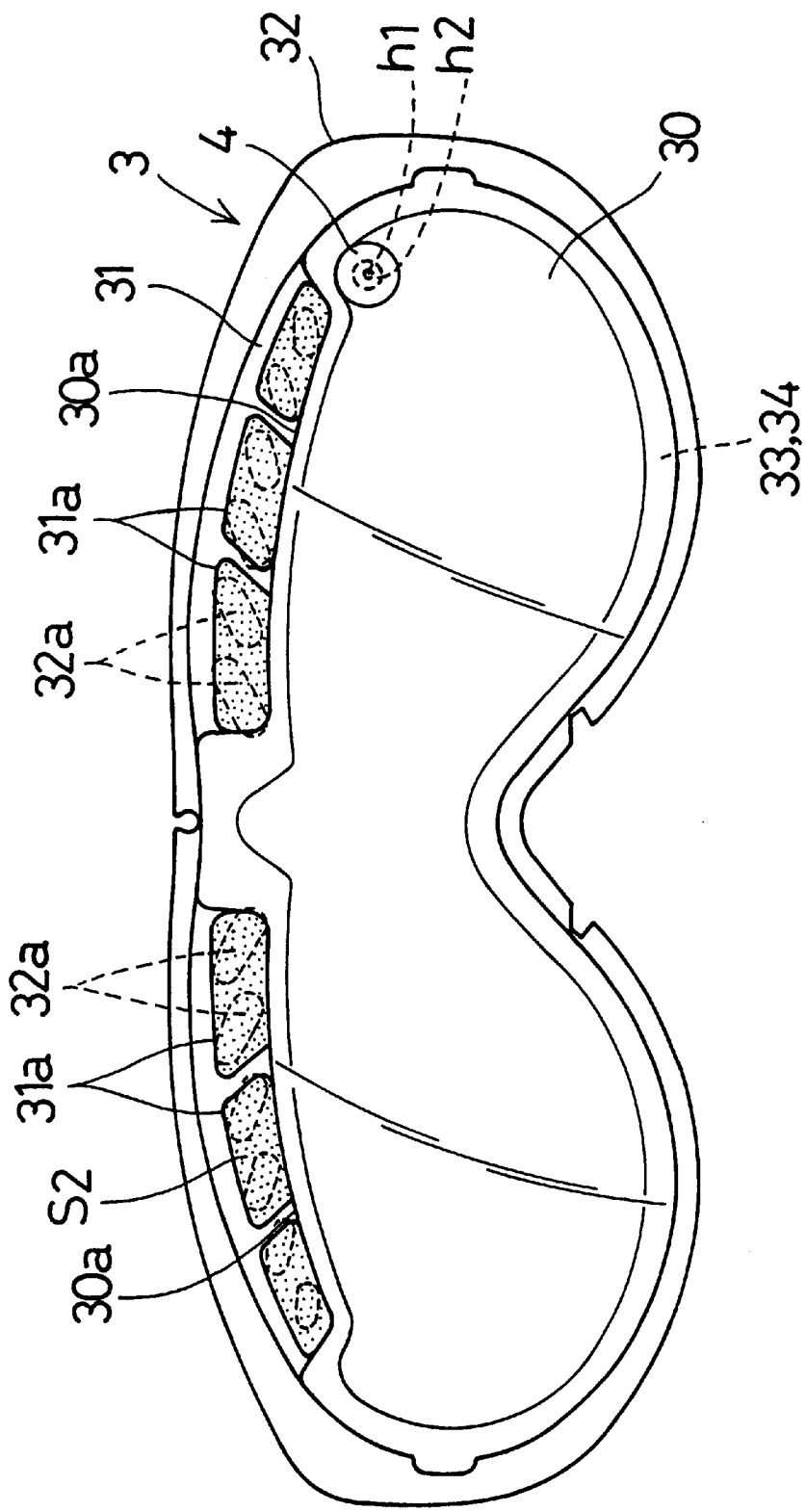
FIG. 5 is a view of goggle lens used in the goggles, which is seen from a side of the inner lens plate.

FIG. 1 is a perspective view of skiing goggles G. FIG. 5 is a view of a goggle lens used in the goggles G seen from a side of an inner lens plate 30. As shown in FIGS. 1 and 2, the goggles G include a goggle frame 1, an expandable, elastic band 2 coupled to the goggle frame 1, a goggle lens 3 detachably fitted into the goggle frame 1 and moisture blocking means 4 attached to the goggle lens 3.

Figure 3:
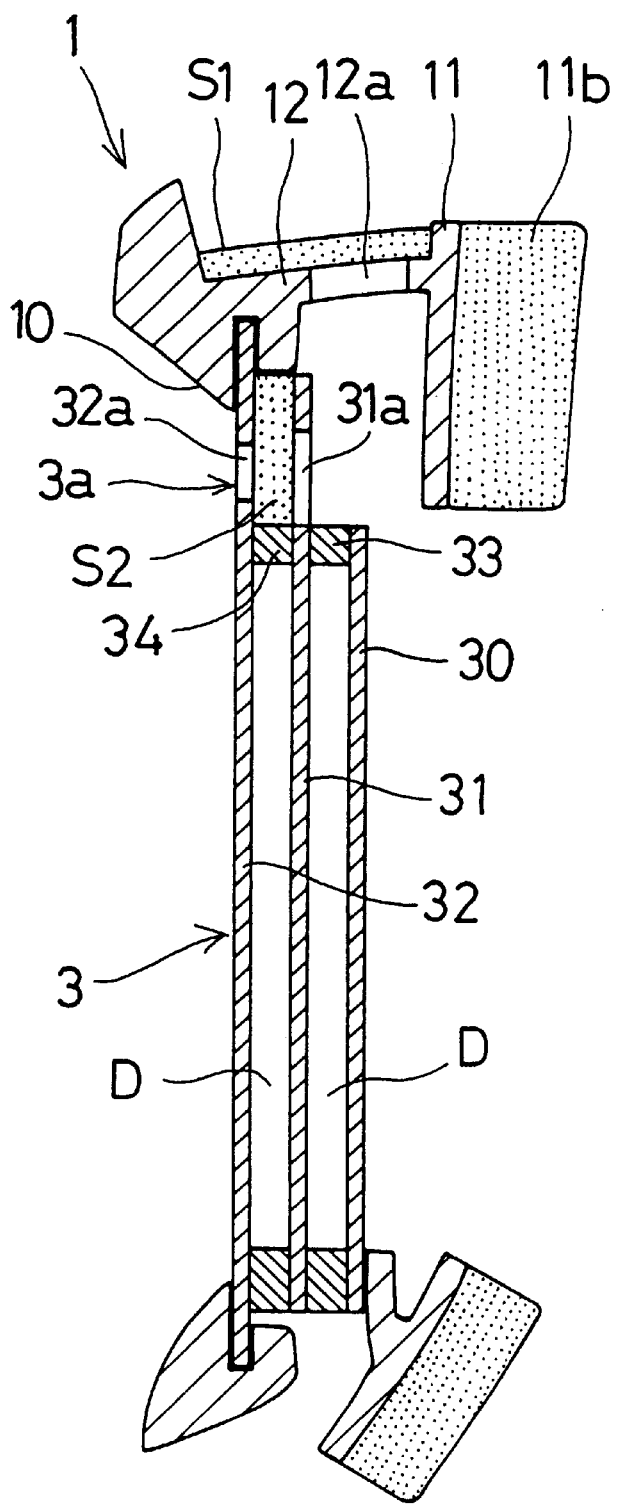
FIG. 3 is a cross-sectional view taken along line A—A of FIG. 2.

The goggle frame 1 is made of soft material such as an elastic synthetic resin, rubber or the like. As shown in FIGS. 1 and 3, the goggle frame 1 has a lens fitting edge 10, a face abutment section 11, and a peripheral wall section 12 connecting the lens fitting edge 10 and the face abutment section 11. The goggle lens 3 is detachably fitted in the lens fitting edge 10.

The face abutment section 11, as shown in FIGS. 2 and 3, is provided with a perforated coupling section 11a for receiving the expandable, elastic rubber band 3 at the both side portions thereof. Also, a close contact material 11b such as sponge or monte plane is bonded to the face abutment section 11 so as to provide a comfortable fitting with a wearer's face.

The peripheral wall section 12 is clearly shown in FIGS. 1 to 3. The vertical and horizontal constitution walls of the peripheral wall section 12 are provided with holes to form ventilation sections 12a, 12b and 12c. These ventilation sections 12a, 12b and 12c are closed by and covered with a thin sponge plate S1 or the like. The reason for closing and covering the. ventilation sections 12a, 12b and 12c by the sponge plate S1 or the like is to prevent snow and/or dust other than air from entering inside of the goggles.

The expandable, elastic band 2 is shown in FIG. 1, and has main bodies 20 and 20 constituted expandable. The band main bodies 20 and 20 are attached to the coupling sections 11a and 11a and coupled with each other through a buckle 21.

As shown in FIGS. 3 and 5, the goggle lens 3 includes of three transparent or color plastic lens plates; inner, intermediate and outer lens plates 30, 31 and 32, and between the peripheral edges of respective adjacent lenses 30, 31 and 32 are interposed spacing frames 33 and 34. The spacing frames 33, 34 and the lens plates holding the frames therebetween are bonded together with an adhesive double coated tape. In this embodiment, the distance between the inner and intermediate lens plates 30 and 31 and that between the intermediate and outer lens plates 31 and 32 are respectively 2 mm. The space between the inner and intermediate lens plates 30 and 31 and that between the intermediate and outer lens plates 31 and 32 function as heat insulating layers D. Also, the thickness of each of the inner, intermediate and outer lens plates 30, 31 and 32 is about 0.6 mm.

The inner lens plate 30 has two concave portions 30a on an upper edge thereof, as shown in FIGS. 3 and 5, and the surface which faces a wearer's face is given anti-fog treatment.

The intermediate lens plate 31 is also shown in FIGS. 3 and 5, and has a shape similar to that of the foregoing inner lens plate 30, but for the two concave portions 30a. The intermediate lens plate 31 is larger than the inner lens plate 30 due to no concave portions 30a and enlarged portions corresponding to the concave portions 30a are provided with holes 31a to form ventilation sections 3a. No treatment is applied to both the sides of the intermediate lens plate 31 so as to ensure the adhesive property of the adhesive double coated tape.

The outer lens plate 32, as shown in FIGS. 3 and 5, is a size larger than the intermediate lens plate 31 and provided with holes 32a constituting the ventilation sections 3a in portions facing the foregoing holes 31a. The outer peripheral edge of the outer lens plate 32 serves as a portion fitted into the lens fitting edge 10. A so-called UV coat or hard coat is applied to the outside surface of the outer lens plate 32 so as to avoid ultraviolet rays.

A sponge plate S2 is disposed between the intermediate lens plate 31 and the outer lens plate 32 and at portions corresponding to the foregoing concave portions 30a and 30a. The reason for providing the sponge plate S2 is the same as that for providing the sponge plate S1 stated above.

Figure 4:
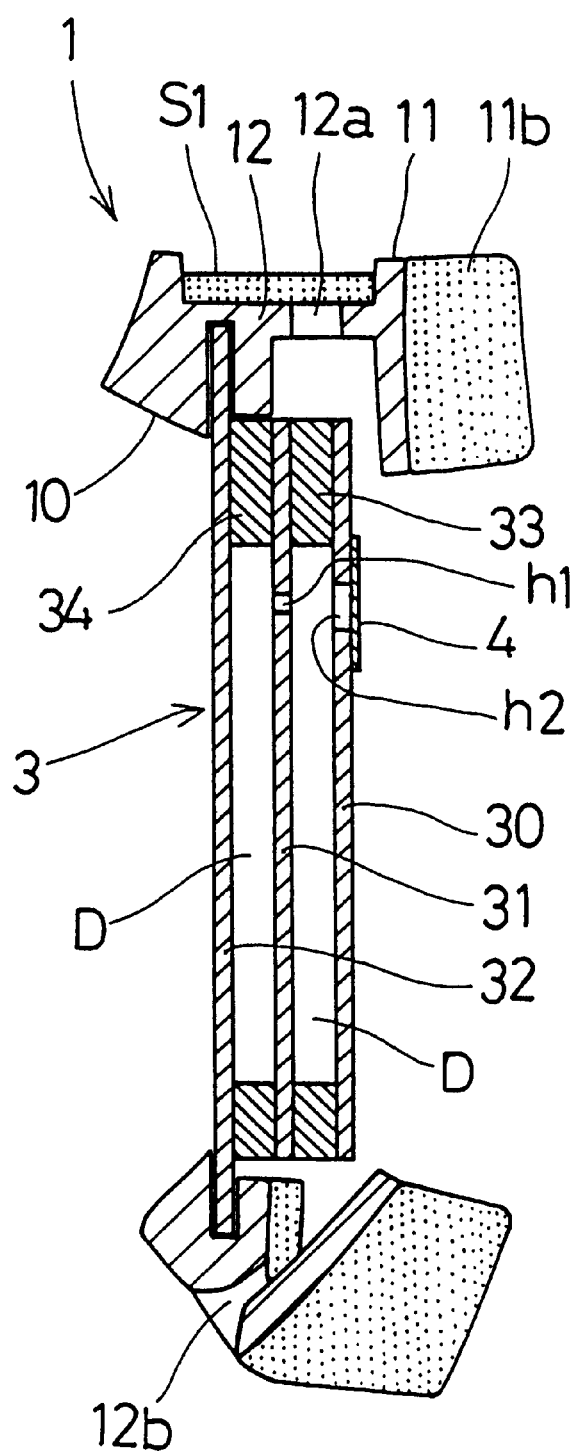
FIG. 4 is a longitudinal sectional view of a constitutional portion of the goggles to which moisture blocking means is bonded.

Further, in this embodiment of the goggles, as shown in FIGS. 4 and 5, a through hole h1 is formed in the neighborhood of the outer edge of the intermediate lens plate 31 where the field of vision is not disturbed and a vent hole h2 is formed in a portion of the inner lens plate 30 facing the through hole h1. As shown in FIG. 4, the vent hole h2 is closed with the moisture blocking means 4.

As the moisture blocking means 4, a water-repellant vent sheet which prevents moisture from entering and permits air to pass is employed. This water-repellant vent sheet is made of a sheet of air-permeable base material such as nylon cloth to which continuous porous material such as tetrafluoroethylene resin fiber layer is bonded. The tetrafluoroethylene resin fiber layer has a drawn, very tough, ductile and fine fiber structure. The layer has many continuous pores, high water-repellency, a mean pore diameter of 0.2 to 5.0$\mu$, a porosity of 25 to 95% and an air flow rate of 0.1 to 3,000 (488 inH$_2$O) cc/sin/in$^2$.

Therefore, when outside air pressure changes due to sliding or the like, the water-repellent vent sheet as the moisture blocking means 4 functions to allow the inside and outside pressures of the goggle lens 3 to be balanced. Thus, the inner, intermediate and outer lens plates 30, 31 and 32 have no deformations and the distortion of the field of vision can be prevented.

Further, when outside air pressure increases, outside air flows in from the vent hole h2 through the water-repellent vent sheet. However, the foregoing water-repellent vent sheet prevents moisture from entering into the inside of the goggle lens 3 even if the outside air contains a large quantity of moisture or even if snow or the like adheres to the outer surface of the air-permeable base material. Therefore, despite the vent hole h2 for balancing pressure, cloud up inside of the goggle lens 3 can be prevented.

Figure 6:
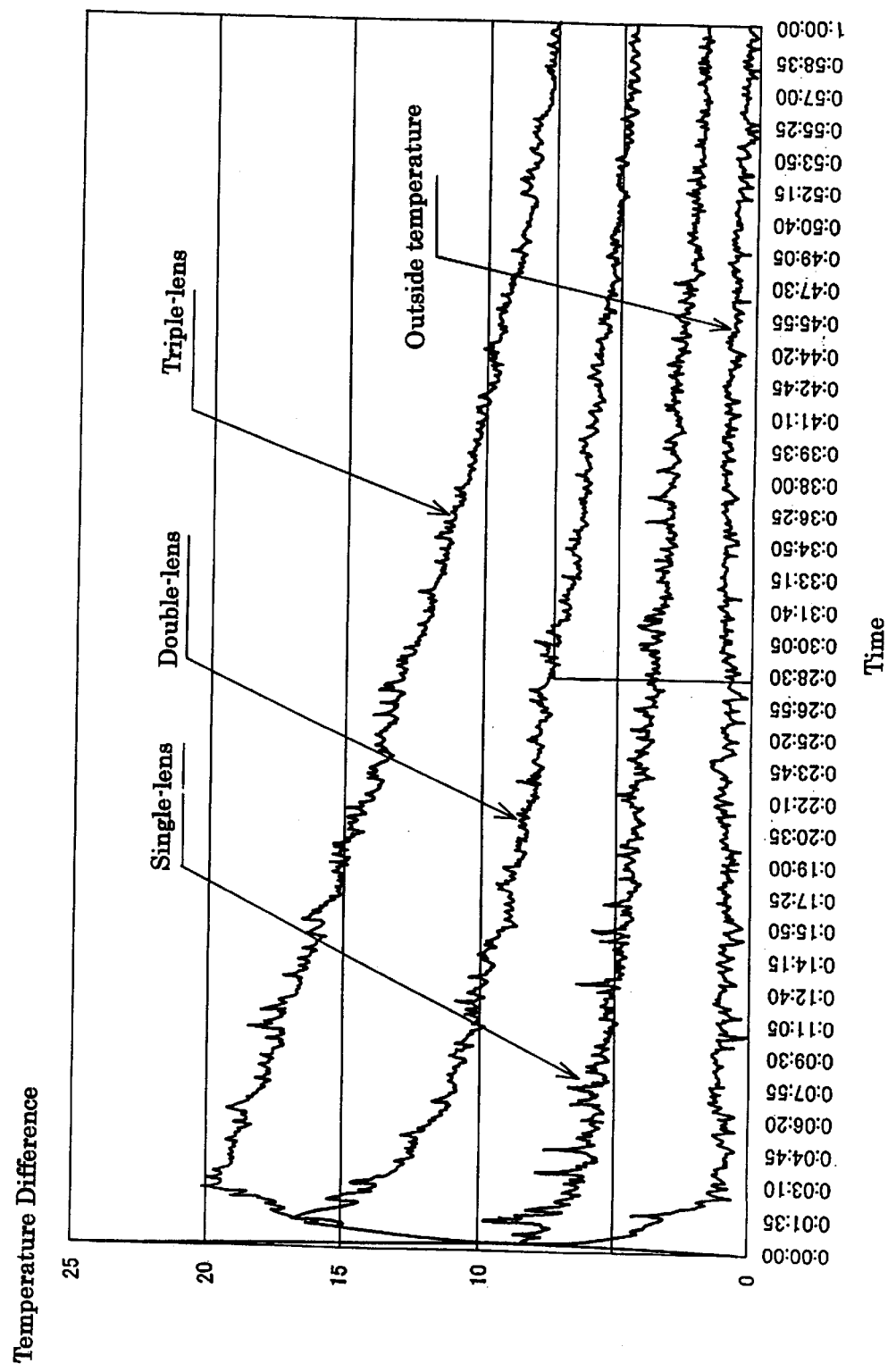
FIG. 6 is a graph showing the temperature differences between inside and outside of the lenses so as to compare the function of the goggles according to the present invention, single-lens goggles and double-lens goggles.

FIG. 6 is a graph showing the temperature differences between the inside and outside of goggle lenses with the passage of time. This graph is depend on the following measurement; heating a human head model at 50° C. for 1 hour, leaving the goggles in a greenhouse, putting the heated model wearing the goggles into in a low temperature tank at 0° C. and then measuring the inside and outside temperatures of the goggle lenses. A so-called double lens having of two (inner and outer) lens plates has a distance of 3 mm between the inner lens plate and the outer lens plate.

The following respects become apparent from the graph of FIG. 6.

(a) Since single-lens goggles do not have a heat insulating layer, the temperature of the inside surface of the lens facing the model's face decreased close to outside air temperature at a high speed. After about 30 minutes, the temperature lowered to 3.5° C., and after 1 hour, to 1.9° C.

The notable point of this graph is that, in case of the single-lens goggles, the temperature inside of the lens suddenly decreased within 1 minute after the goggles were put in the low temperature tank.

(b) The double-lens goggles have a heat insulating layer of 3 mm and, therefore, the inner side temperature of the lens facing the model's face became close to outside air temperature at a relatively slow speed compared with (a). After about 30 minutes, the temperature lowered to 7.5° C., and after 1 hour, to 4.5° C. Here, it is notable in this graph that, in case of the double-lens goggles, despite the heat insulating layer with a thickness of 3 mm, the inner side temperature of the lens sharply decreased within about 15 minutes after the goggles were put in the low temperature tank. Namely, it lowered to 13° C. after 3 minutes and to 9° C. after 15 minutes.

(c) The three-lens goggles in the embodiment of the present invention have two heat insulating layers with a thickness of 2 mm. The temperature of the inside surface of the lens facing the model's face decreased close to outside air temperature at a slow speed. Even after 1 hour, the temperature of the inside surface of the lens was as high as 7.4° C. Here, it is notable in this graph that, in case of this embodiment, the temperature of the inside surface of the inner lens plate 39 of the goggle lens 3 was as high as 20° C. in 3 minutes after the goggles were put in the low temperature tank and as high as 16° C. even in 15 minutes thereafter.

(d) In goggles, the lower the temperature of the inner surface of the goggle lens facing a wearer's face is, the easier the inner surface becomes clouded up and water drops thereon become frozen. It is, therefore, quite apparent that the inner surface of the goggles of a single-lens structure tends to be clouded up and water drops thereon tend to be frozen. It is also apparent that the anti-fog effect and the water drop deicing effect of the goggles G having three lenses according to this embodiment are far more superior to those of the goggles having two lenses.

(e) Moreover, in case of a goggle lens plate with a thickness of 0.6 mm, the goggle lens 3 of this embodiment is about 1.4 times as thick as the goggle lens with two lenses (the former thickness: 5.8 mm, the latter thickness: 4.2 mm). However, as stated above, the anti-fog effect and the water drop deicing effect of the goggles G of this embodiment are superb and the distance between the inner lens plate 30 and a wearer's face is only about 1.6 mm, and the goggles G will not give uncomfortable fitting.

The present invention should not be limited to the above-mentioned embodiment. In place of the vent hole h2 provided in the inner lens plate 30, a vent hole h2 may be provided at a position of the outer lens plate 32 where the field of vision is not disturbed. Alternatively, vent holes h2 may be provided both in the inner and outer lens plates 30 and 32. The vent hole or holes h2 are preferably closed with the moisture blocking means 4 like the above-stated embodiment. Besides, in order to prevent the moisture blocking means 4 from peeling off due to sweat or the like, the moisture blocking means 4 may be preferably bonded to the side of the inner lens plate 30 facing the intermediate lens plate 31.

Alternatively, without providing the through hole h1 in the intermediate lens plate 31, vent holes h2 may be formed at positions of both the inner and outer lens plates 30 and 32 where the field of vision is not disturbed, and the vent holes 2 may be closed by the moisture blocking means 4. In this case, in order to prevent the moisture blocking means 4 from peeling off due to sweat or the like, it is preferable to bond the moisture blocking means 4 to the side of the inner lens plate 30 which faces the intermediate lens plate 31.

In the goggles according to the present invention, each distance between two adjacent lens plates can be set within the range of 1.6 to 2.4 mm.

Furthermore, the goggles according to the present invention should not be limited to skiing goggles. The goggles may be used for other purposes, such as dust-proof goggles or goggles for cold whether regions.

With the constitution stated above, the present invention has the following advantage. As clear from the section of "Description of Preferred Embodiments", the present invention can provide goggles which prevent water drops on an inner surface of goggle lens from easily being frozen and produce a highly improved anti-fog effect if the temperature of the surface of the goggle lens is below 0° C.

What is claimed is:

1. Goggles comprising an inner lens plate, an intermediate lens plate, an outer lens plate, a first space between said inner and intermediate lens plates, and a second space between said intermediate and outer lens plates and wherein said first space between said inner and intermediate lens plates and said second space between said intermediate and outer lens plates form heat insulating layers, and wherein said intermediate lens plate has a through hole, at least one of said inner and outer lens plates has a vent hole, and said vent hole is covered with a moisture blocking means which prevents moisture from passing and allows air to pass.

2. Goggles according to claim 1, wherein a distance between adjacent lens plates is from 1.6 to 2.4 mm.

3. Goggles according to claim 1, wherein said through hole and said vent hole are provided at positions where a field of vision is not disturbed.

4. Goggles comprising an inner lens plate, an intermediate lens plate, an outer lens plate, a first space between said inner and intermediate lens plates, and a second space between said intermediate and outer lens plates and wherein said first space between said inner and intermediate lens plates and said second space between said intermediate and outer lens plates form heat insulating layers, and wherein said intermediate lens plate has a through hole, said inner lens plate has a vent hole and said vent hole is covered with a moisture blocking means which prevents moisture from passing and allows air to pass.

5. Goggles according to claim 4, wherein a distance between adjacent lens plate is 2 mm.

6. Goggles according to claim 5, wherein said through hole and said vent hole are provided at positions where a field of vision is not disturbed.

7. Goggles according to claim 4, wherein said through hole and said vent hole are provided at positions where a field of vision is not disturbed.

8. Goggles comprising an inner lens plate, an intermediate lens plate, an outer lens plate, a first space between said inner and intermediate lens plates, and a second space between said intermediate and outer lens plates and wherein said first space between said inner and intermediate lens plates and said second space between said intermediate and outer lens plates form heat insulating layers, and wherein each of said inner and outer lens plate has a vent hole and said vent hole is coverd with a moisture blocking means which prevents moisture from passing and allows air to pass.

9. Goggles according to claim 8, wherein spacing frames are respectively provided between said inner and intermediate lens plates and between said intermediate, and outer lens plates and contacting faces between said inner, intermediate and outer lens plates and said spacing frames are bonded together.

10. Goggles according to claim 9, wherein said vent hole is provided at a position where a field of vision is not disturbed.

11. Goggles according to claim 8, wherein said vent hole is provided at a position where a field of vision is not disturbed.

12. Goggles according to claim 2, wherein said through hole and said vent hole are provided at positions where a field of vision is not disturbed.

* * * * *